United States Patent [19]
Azuma et al.

[11] Patent Number: 5,200,190
[45] Date of Patent: Apr. 6, 1993

[54] PERCUTANEOUS PHARMACEUTICAL PREPARATION

[75] Inventors: Masato Azuma, Osaka; Hiroko Tsukahara, Takatsuki; Hiroshi Kuroda, Ibaraki; Mutsumi Fukuda, Osaka, all of Japan

[73] Assignee: Sekisui Kagaku Kogyo Kabushiki Kaisha, Osaka, Japan

[21] Appl. No.: 419,356

[22] Filed: Oct. 10, 1989

[30] Foreign Application Priority Data

| Oct. 11, 1988 | [JP] | Japan | 63-256379 |
| Jan. 26, 1989 | [JP] | Japan | 1-16622 |
| Mar. 7, 1989 | [JP] | Japan | 1-54779 |
| Jun. 14, 1989 | [JP] | Japan | 1-150986 |
| Jul. 10, 1989 | [JP] | Japan | 1-178537 |
| Jul. 10, 1989 | [JP] | Japan | 1-178538 |

[51] Int. Cl.$^5$ ............................................. A61F 13/02
[52] U.S. Cl. ............................... 424/443; 424/448; 424/449; 424/447
[58] Field of Search ..................... 424/448, 449, 443

[56] References Cited

U.S. PATENT DOCUMENTS 4,751,087  6/1988  Wick .................................. 424/448
4,818,540  4/1989  Chien et al. ....................... 424/449

FOREIGN PATENT DOCUMENTS

0156080  10/1985  European Pat. Off. .
0181970   5/1986  European Pat. Off. .
57-154122  9/1982  Japan .
61-155321  7/1986  Japan .

Primary Examiner—Thurman K. Page
Assistant Examiner—Leon R. Horne
Attorney, Agent, or Firm—Armstrong & Kubovcik

[57] ABSTRACT

A percutaneous pharmaceutical preparation in tape form is provided. The preparation comprises a flexible backing, which is not permeable to an active ingredient, and an adhesive layer formed on the flexible backing, the adhesive layer comprising an adhesive base material and an active ingredient compatible with the adhesive base material, wherein the adhesive base material consists essentially of a copolymer containing 2-ethylhexyl acrylate in a concentration of 45 to 80 mol % and N-vinyl-2-pyrrolidone in a concentration of 20 to 55 mol %, and the active ingredient is estradiol and/or the esters thereof which are contained in a concentration of 6 to 25% by weight of the total amount of the adhesive base material and the active ingredient.

10 Claims, 7 Drawing Sheets

PERCUTANEOUS PHARMACEUTICAL PREPARATION

BACKGROUND OF THE INVENTION

1. Field of the Invention

The present invention relates to a percutaneous pharmaceutical preparation in tape form that contains estradiol and/or the esters thereof as active ingredients and permits administration of the said active ingredients by percutaneous absorption. In particular, the present invention relates to a percutaneous pharmaceutical preparation in tape form that is excellent in both release and transfer via the skin of the active ingredients, and that can provide sustained stable concentrations of the said active ingredients in the blood.

2. Description of the Prior Art

Estradiol and its esters are known as a type of female hormone which is effective for pharmacological treatment of gynecological disorders such as climacteric disturbances and menstrual abnormalities. However, owing to a high rate of hepatic metabolization, the oral administration of these drugs places a severe load upon the liver, and metabolization markedly reduces the bioavailability of the drug. Therefore, this type of drug is ordinarily administered by injection. However, although injection induces a transient elevation of the drug concentration in blood, the said concentration is not sustained over a long period, and consequently frequent administration is necessary. Hence, the use of pharmaceutical preparations with slow release is desirable, for example, preparations of a percutaneous administration type are regarded as appropriate for this purpose. However, because the skin possesses the function of preventing the intrusion of foreign matter into the body, the administration of adequate amounts of drugs by the percutaneous route is generally difficult. In order to cope with this difficulty, the area of percutaneous pharmaceutical preparation in tape form is enlarged, or various agents which accelerate percutaneous absorption are included in the preparation. Nevertheless, the drug release capabilities of such preparations cannot be regarded as adequate.

For achieving more effective percutaneous administration of estradiol or its esters, a multilayered pharmaceutical preparation is proposed in Japanese Laid-Open Patent Publication No. 57-154122. This preparation consists of a backing upon which are successively superimposed a layer that contains an active ingredient, a diffusion membrane and a pressure sensitive adhesive layer. The layer containing an active ingredient is composed of a drug gel containing estradiol dispersed in a gel formed by gelation of hydroxypropyl cellulose, etc., with ethanol. The active ingredient together with the ethanol penetrate the diffusion membrane and the pressure sensitive adhesive layer, and are then absorbed through the skin. Ethanol penetrates the skin at the rate of approximately 100–800 mcg/hr/cm$^2$, and therefore the percutaneous absorption of the active ingredient dissolved in the ethanol is enhanced. Thus, the release of the active ingredient can be controlled by adjusting the amount of ethanol used, etc. However, because this type of preparation is multilayered, the manufacturing process of the preparation is complex, moreover, owing to the thickness of the patch, attachment to the skin causes an unpleasant feeling. Furthermore, owing to the volatility of the ethanol used, the capability of releasing the active ingredient changes during storage or after attachment of the preparation, and the releasing capability decreases with time after attachment of the preparation. Also, because ethanol irritates the skin, attachment of such a preparation is likely to cause dermal symptoms such as erythema, etc. Furthermore, due to the interposition of the diffusion membrane that functions as a control membrane, the release of ethanol and the active ingredient is insufficient, and a comparatively large area of the preparation is necessary in order to achieve satisfactory pharmacological effect.

Japanese Laid-Open Patent Publication No. 61-155321 discloses a percutaneous pharmaceutical preparation, in which an adhesive layer containing estradiol is formed on a backing, the principal components of the adhesive base material in the adhesive layer being rubber, an adhesive resin material and a polymer such as galactomannan which swells in water. This type of preparation is not unduly bulky like the above-mentioned multilayered preparation, and can provide a relatively stable delivery of the active ingredient over a prescribed period of time. Nevertheless, the overall drug-releasing capability of this preparation still cannot be regarded as adequate.

SUMMARY OF THE INVENTION

The percutaneous pharmaceutical preparation of this invention, which overcomes the above-discussed and numerous other disadvantages and deficiencies of the prior art, comprises a percutaneous pharmaceutical preparation comprising a flexible backing, which is not permeable to an active ingredient, and an adhesive layer formed on said flexible backing; said adhesive layer comprising an adhesive base material and an active ingredient compatible with said adhesive base material, wherein said adhesive base material consists essentially of a copolymer containing 2-ethylhexyl acrylate in a concentration of 45 to 80 mol % and N-vinyl-2-pyrrolidone in a concentration of 20 to 55 mol %, and said active ingredient is estradiol and/or the esters thereof which are contained in a concentration of 6 to 25% by weight of the total amount of said adhesive base material and said active ingredient.

In a preferred embodiment, the copolymer contains 2-ethylhexyl acrylate in a concentration of 55 to 70 mol %, and N-vinyl-2-pyrrolidone in a concentration of 30 to 45 mol %.

In a preferred embodiment, the adhesive layer contains a percutaneous absorption accelerating agent.

In a preferred embodiment, the accelerating agent comprises an ester of higher fatty acid obtained from a higher fatty acid with 10 to 18 carbon atoms and an alcohol with 1 to 20 carbon atoms.

In a preferred embodiment, the accelerating agent comprises a compound containing at least one amide bond.

In a preferred embodiment, the accelerating agent comprises an ester of lactic acid obtained from lactic acid and an alcohol with 1 to 20 carbon atoms.

In a preferred embodiment, the accelerating agent comprises lactic acid and/or the salts thereof.

In a preferred embodiment, the accelerating agent comprises a dicarboxylic acid with 2 to 10 carbon atoms and/or the salts thereof.

In a preferred embodiment, the dicarboxylic acid is fumaric acid.

In a preferred embodiment, the accelerating agent comprises citric acid and/or the salts thereof.

In a preferred embodiment, the accelerating agent comprises O-alkyl-(polyoxyethyl) phosphate and/or the salts thereof.

Thus, the invention described herein makes possible the objectives of:

(1) providing a percutaneous pharmaceutical preparation in tape form containing estradiol and/or the esters thereof as an active ingredient such that the cutaneous permeation of the said active ingredients is high, permitting the delivery of sufficient doses even with a small patch area;

(2) providing a percutaneous pharmaceutical preparation in tape form with the superior characteristics stated above and without dermal irritation;

(3) providing a percutaneous pharmaceutical preparation in tape form of simple structure which simplifies the manufacturing process; and (4) providing a percutaneous pharmaceutical preparation in tape form which undergoes no changes in composition and maintains its specified quality during storage.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

The principal component of the adhesive base material of the adhesive layer used in the preparation of this invention is a copolymer containing 2-ethylhexyl acrylate (EHA) and N-vinyl-2-pyrrolidone (VP) as polymer components. The content of EHA in this copolymer ranges from 45 to 80 mol %, and preferably 55 to 70 mol %, while the content of VP ranges from 20 to 55 mol %, and preferably 30 to 45 mol %. If the proportion of EHA is excessive and the proportion of VP is unduly low, then the solubility of the estradiol and/or the esters thereof decreases. Conversely, if the proportion of VP is excessive and the proportion of EHA is unduly low, then the adhesiveness decreases and the preparation cannot be securely attached to the skin. In accordance with various needs, acrylates and/or methacrylates other than 2-ethylhexyl acrylate may also be included in the constituents of the copolymer. These (meth)acrylates preferably contain 6 to 16 carbon atoms, the examples of which include propyl (meth)acrylate, butyl (meth)acrylate, hexyl (meth)acrylate, 2-ethylbutyl (meth)acrylate, heptyl (meth)acrylate, octyl (meth)acrylate, nonyl (meth)acrylate, decyl (meth)acrylate, and lauryl (meth)acrylate. The content of the (meth)acrylates should be 35 mol % or less, and more preferably 15 mol % or less. If the proportion of the (meth)acrylates is excessive, then high concentrations of estradiol or its esters cannot be present in the adhesive layer in a dissolved state. Also, in order to improve the internal cohesive properties of the copolymer, a multifunctional monomer is preferably included in the proportion of 0.005 to 0.5% by weight of the total amount of monomer constituents of the copolymer. The applicable multifunctional monomers include di(meth)acrylates, tri(meth)acrylates and tetra(meth)acrylates, for example, hexamethyleneglycol dimethacrylate, trimethylolpropane triacrylate, etc.

The active ingredient in the percutaneous pharmaceutical preparation of the present invention are estradiol and/or the esters thereof. The esters of estradiol include benzoate, valerate, cipionate, and propionate, etc. For the total weight of the adhesive layer to be described below (i.e., total weight of the adhesive base material, active ingredient and, when necessary, percutaneous absorption accelerating agent, etc.), the proportion of this active ingredient should be from 6 to 25% by weight, preferably, 8 to 20% by weight, and still more preferably, 10 to 14% by weight. If this proportion is unduly low, then the effect the active ingredient is insufficient, and if excessive, then the said active ingredient may crystallize within the adhesive base material and not be adequately released.

A percutaneous absorption accelerating agent may also be added to the adhesive base material as is required. As the percutaneous absorption accelerating agent, at least one selected from the following group of compounds is particularly useful; compounds containing at least one amide bond, esters of lactic acid, lactic acid, salts of lactic acid, dicarboxylic acids, salts of dicarboxylic acids, citric acid, salts of citric acid, O-alkyl(polyoxyethyl)phosphates and esters of higher fatty acids.

Among the above-mentioned compounds containing at least one amide bond which can be used for the present invention are N-acylsarcosine, fatty acid ethanol amides, etc. The number of carbon atoms in the acyl group of the said N-acylsarcosine should preferably be from 6 to 18. For example, N-lauroylsarcosine is suitable for the present purpose. Either mono- or diethanol amides may be employed as the above-mentioned fatty acid ethanol amide. The alkylene-oxide adducts of these compounds can also be used. The fatty acid components of the aforesaid fatty acid ethanol amides should preferably contain 12 to 16 carbon atoms. The compounds containing at least one amide bond include, N-(2-hydroxyethyl)lauramide, N-(2-hydroxyethyl)palmitamide, N,N-di(2-hydroxyethyl)myristamide, a mixture of N,N-di(2-hydroxyethyl)lauramide and N,N-di(2-hydroxyethyl)myristamide, coconut oil fatty acid monoethanol amide, N-(polyoxyethylene ethanol)lauramide, polyoxyethylene adducts of coconut oil fatty acid monoethanol amide, N,N-di(2-hydroxyethyl)lauramide, coconut oil fatty acid diethanol amide, N,N-di(polyoxyethylene ethanol)lauramide and polyoxyethylene adducts of coconut oil fatty acid diethanol amide. The appropriate mole number of polyoxyethylene in the aforesaid polyoxyethylene adducts is 1 to 40. Here, the mole number 1 indicates that, in the case of monoethanol amides, 1 molecule of alkylene oxide, and in the cases of diethanol amides, 2 molecules of alkylene oxide are to be added for each molecule of ethanol amide. These compounds with amide bonds should be added 30 parts by weight or less, and more preferably, 0.05 to 30 parts by weight for every 100 parts by weight of the aforesaid adhesive base material.

The esters of lactic acid among the aforesaid percutaneous absorption accelerating agents are obtained from lactic acid and an alcohol with 1 to 20 carbon atoms. Such esters include, myristyl lactate, cetyl lactate, etc.

The ester of lactic acid is added 30 parts by weight or less, preferably, 0.5 to 30 parts by weight, and more preferably, 1 to 10 parts by weight for every 100 parts by weight of the aforesaid adhesive base material.

The applicable salts of lactic acid include, for example, sodium lactate, potassium lactate, calcium lactate, etc. The lactic acid and/or salts of lactic acid are added 30 parts by weight or less, preferably, 0.1 to 30 parts by weight, and more preferably, 3 to 7 parts by weight, for every 100 parts by weight of the aforesaid adhesive base material.

The dicarboxylic acids which can be used as the percutaneous absorption accelerating agent should have 2 to 10 carbon atoms. Salts of these dicarboxylic acids can equally well be used. The dicarboxylic acids include oxalic acid, malonic acid, fumaric acid, maleic acid, tartaric acid, malic acid, succinic acid, glutaric acid, adipic acid, phthalic acid, isophthalic acid and terephthalic acid, etc. The applicable salts of these acids include sodium, potassium, magnesium, calcium and aluminum salts, etc. Fumaric acid and/or its salts are especially suitable. The dicarboxylic acids and/or the salt thereof are added 30 parts by weight or less, preferably, 0.1 to 30 parts by weight, and more preferably, 3 to 7 parts by weight, for every 100 parts by weight of the aforesaid adhesive base material.

The O-alkyl(polyoxyethyl) phosphates which can be used as the percutaneous absorption accelerating agent are obtained by esterification of polyoxyethylene alkyl ether by use of phosphoric acid, the said polyoxyethylene alkyl ether being obtained by addition of ethylene oxide to alcohols. The amount of ethylene oxide added should be 2 to 10 molecules per molecule of alcohol. The appropriate number of carbon atoms in the alkyl group of the polyoxyethylene alkyl ether (i.e., the alkyl group of the aforesaid alcohol) is 1 to 20. The alkyl group includes methyl, ethyl, propyl, butyl, pentyl, hexyl, heptyl, octyl, nonyl, decyl, dodecyl, lauryl, stearyl, palmityl myristyl, isopropyl, cetyl, t-butyl, etc. O-Lauryl(tetraoxyethyl) phosphate and/or the salts thereof are especially suitable. The applicable salts of these compounds include sodium, potassium, magnesium, calcium salt, and the like. The aforesaid O-alkyl(polyoxyethyl) phosphates (including their salts) are added 30% by weight or less, preferably, 0.1 to 30% by weight, and more preferably, 1 to 20% by weight, of the total weight of the adhesive material.

The higher fatty acid esters which can be used as the percutaneous absorption accelerating agent are obtained from higher fatty acids with 10 to 18 carbon atoms and alcohols with 1 to 20 carbon atoms. The percutaneous absorption accelerating effect is particularly improved if the compound is used in combination with at least one of the various percutaneous absorption accelerating agents mentioned previously. The esters of higher fatty acid applicable for the present purpose include isopropyl myristate, isopropyl palmitate, etc., isopropyl myristate being especially desirable. The ester of higher fatty acid is added 80 parts by weight or less, and preferably, 1 to 80 parts by weight for each 100 parts by weight of the aforesaid adhesive base material.

If the amount of these absorption accelerating agents is excessively large, then the absorption accelerating agents cannot be present in the adhesive base material in a dissolved state, resulting in poor adhesiveness.

As regards the backing of the preparation, the types of backing ordinarily employed for medicinal patches, impermeable to the drug, may be used for the present invention. The raw materials applicable for these backings include cellulose acetate, ethyl cellulose, polyethylene terephthalate, vinyl acetate-vinyl chloride copolymers, nylon, ethylene-vinyl acetate copolymers, plasticized polyvinyl chloride, polyurethane, polyethylene, polyvinylidene chloride and aluminum, etc. These materials can be used in the form of either a single-layer sheet (film) or a laminate of two or more layers.

The percutaneous pharmaceutical preparation of the present invention is obtained by the formation of an adhesive layer on the surface of the aforesaid backing, the adhesive layer being a mixture consisting of the adhesive base material plus estradiol and/or the esters thereof and, if necessary, a percutaneous absorption accelerating agent and/or other additives. Various coating processes may be employed for the formation of the said adhesive layer, including the solvent coating processes, hot melt coating processes, etc.; among these, the solvent coating method is particularly suitable for the present purpose. In order to form the adhesive layer by the solvent coating process, for example, the adhesive base material is diluted with a suitable solvent, then the aforesaid active ingredient, and, if necessary, an absorption accelerating agent and/or other additives are added, these ingredients are uniformly mixed, and the resulting solution is coated onto the backing and dried. Alternatively, rather than coating the solution directly onto the surface of the backing, the solution is first coated onto a release paper precoated with silicone resin, and after drying, the coated release paper is fastened onto the backing. The thickness of the adhesive layer is not restricted, but ordinarily the thickness ranges from 30 to 200 $\mu$m.

The adhesive base material employed in the present invention is capable of dissolving estradiol and/or the esters thereof in a high concentration. Consequently, the quantity of the active ingredient released per unit area and per unit time as well as the rate of transfer of the active ingredient through the skin and into the subdermal tissue are extremely high. Also, when the preparation is applied to the skin, excellent control is obtained, i.e., the said active ingredients contained in the preparation are released at prescribed rates over a prolonged period of time. Thus, as compared with previous types of preparations for the administration of estradiol, the preparation of this invention provides greater effective doses for a given area, or, equivalently, the preparation of this invention can provide the same drug administration effect as previous types with a smaller area.

If a percutaneous absorption accelerating agent is also included in the adhesive layer, then the rate of transfer of the drug into the subdermal zone is even higher (i.e., drug release is further improved). This is attributed to alteration of the physical properties of the adhesive base material or the skin by the aforesaid absorption accelerating agent, causing a change in the distribution coefficient of the active ingredient between the adhesive layer and the cutaneous tissue, or a change in the diffusion velocity of the active ingredient. Thus, by addition of an absorption accelerating agent, a percutaneous pharmaceutical preparation in tape form is obtained that can maintain a high concentration of the active ingredient in blood for a prolonged period with a small area. By contrast, when conventional adhesive base materials with low drug solubility are used, macroscopically visible crystals of the active ingredient grow in the adhesive layer, and even if the drug is in a supersaturated state when the preparation is produced, growth of the crystals of the active ingredient occurs during storage. When the drug crystallizes, then even the diffusion of a dissolved active ingredient is impeded, and therefore the rate and overall quantity of the release of the active ingredient diminishes. Moreover, the drug is not released at the prescribed rate, and the rate of release decreases with time elapsed after the preparation is applied to the skin.

Furthermore, the adhesive base material used for the present invention is highly hydrophilic, and contains no acidic monomers such as (meth)acrylic acid, and therefore the skin irritation caused by the present type of preparations is greatly reduced. In addition, as stated above, because adequate dosage of the active ingredient can be achieved with a small area, erythema can be avoided even in individuals particularly sensitive to skin irritation. Moreover, because the required area of the preparation is small, the operation of attachment is simple and the unpleasant feeling caused by application of the preparation is decreased. Because the structure of the adhesive layer is monolaminar and simple, the manufacture of the preparation is simplified and the preparation can be produced in a very thin form. Furthermore, the preparation of the present invention does not contain volatile components such as ethanol, which, as pointed out in the foregoing description of prior art, are contained in previously existing types of preparations, and therefore the composition of the preparation of this invention does not change during storage and the prescribed quality of the preparation can be maintained for a prolonged period.

EXAMPLES

The present invention will be described with the following examples.

Example 1

First, 302.0 g (65 mol %) of 2-ethylhexyl acrylate (EHA), 98.0 g (35 mol %) of vinylpyrrolidone (VP) and 40.0 mg (0.01% by weight based on the total weight of the monomers) of hexamethylene glycol dimethacrylate were charged to a flask, and 70.6 g of ethyl acetate was added to obtain a solution with a monomer concentration of 85% by weight. Then, this solution was heated to 60° C. in a nitrogen atmosphere, lauroyl peroxide (as a polymerization initiator) and ethyl acetate were added by small quantities, and the polymerization reaction was carried out for 32 hours, thereby obtaining an ethyl acetate solution of a polymer (i.e., an adhesive material) containing 35% solid content. A tetrahydrofuran solution of 17$\beta$-estradiol was added to the polymer solution obtained above so that the solid content (i.e., the sum of the weights of the polymer and estradiol) would be 22% by weight, and the concentration of estradiol within the solid would be 10.5% by weight. These ingredients were then uniformly mixed in a dissolver. Additional solutions were also prepared in a similar manner so that the concentrations of estradiol would be 12% and 15% by weight, respectively. Each of these solutions was then coated onto release papers having the thickness of 38 $\mu$m consisting of polyethylene terephthalate (PET) film treated with silicone mold-release, respectively, so that the thickness of each coating after drying would be 40 $\mu$m. Each of these coatings was then dried and the desired percutaneous pharmaceutical preparation was obtained by applying a backing of PET film having the thickness of 38 $\mu$m onto the dried coating. The components that form the adhesive layer of the percutaneous preparation obtained in this example as well as those of the preparations obtained in Examples 2-14 and Comparative Examples 1-3, that will be described below, are shown in Table 1.

Example 2

By use of 215.2 g (45 mol %) of EHA, 129.7 g (45 mol %) of VP, 55.1 g (10 mol %) of decyl methacrylate and 40.0 mg (0.01% by weight based on the total weight of the monomer) of trimethylol propane triacrylate, a polymer solution (i.e., a solution of adhesive material) was obtained in the same manner as in Example 1. The same process was repeated as in Example 1 except that the above-mentioned polymer solution was used in place of the polymer solution obtained in Example 1.

Example 3

To the polymer solution (i.e., the solution of adhesive material) obtained in Example 1, 17$\beta$-estradiol and isopropyl myristate were added so that the proportion of solids in the solution (i.e., the sum of the aforesaid constituents and the polymer) would be 25% by weight, and so that within the total solid content, the proportion of 17$\beta$-estradiol would be 10.5% by weight and that of isopropyl myristate would be 5.0% by weight. This mixture was uniformly stirred in a dissolver, and the percutaneous preparation was then obtained by the same process as was used in Example 1.

Example 4

To the polymer solution (i.e., the solution of adhesive material) obtained in Example 1, 17$\beta$-estradiol, N-lauroylsarcosine and isopropyl myristate were added so that the proportion of solids in the solution (i.e., the sum of the aforesaid constituents and the polymer) would be 25% by weight, and so that within the total solid content, the proportion of 17$\beta$-estradiol would be 10.5% by weight, that of N-lauroylsarcosine 3.0% by weight and that of isopropyl myristate 3.0% by weight. This mixture was uniformly stirred in a dissolver, and the percutaneous preparation was then obtained by the same process as was used in Example 1.

Example 5

To the polymer solution obtained in Example 1, 17$\beta$-estradiol and myristyl lactate were added so that the proportion of solids in the solution (i.e., the sum of the aforesaid constituents and the polymer) would be 22% by weight, and so that within the total solid content, the proportion of 17$\beta$-estradiol would be 10.5% by weight and that of myristyl lactate would be 5.0% by weight. This mixture was uniformly stirred in a dissolver, and the percutaneous preparation was then obtained by the same process as was used in Example 1.

Example 6

To the polymer solution (i.e., the solution of adhesive material) obtained in Example 1, 17$\beta$-estradiol myristyl lactate and isopropyl myristate were added so that the proportion of solids in the solution (i.e., the sum of the aforesaid constituents and the polymer) would be 22% by weight, and so that within the total solid content, the proportion of 17$\beta$-estradiol would be 10.5% by weight, that of myristyl lactate 3.0% by weight and that of isopropyl myristate 5.0% by weight. This mixture was uniformly stirred in a dissolver, and the percutaneous preparation was then obtained by the same process as was used in Example 1.

Example 7

To the polymer solution (i.e., the solution of adhesive material) obtained in Example 1, 17β-estradiol and lactic acid were added so that the proportion of solids in the solution (i.e., the sum of the aforesaid constituents and the polymer) would be 22% by weight, and so that within the total solid content, the proportion of 17β-estradiol would be 10.5% by weight and that of lactic acid would be 5.0% by weight. This mixture was uniformly stirred in a dissolver, and the percutaneous preparation was then obtained by the same process as was used in Example 1.

Example 8

To the polymer solution (i.e., the solution of adhesive material) obtained in Example 1, 1762 -estradiol, lactic acid and isopropyl myristate were added so that the proportion of solids in the solution (i.e., the sum of the aforesaid constituents and the polymer) would be 25% by weight, and so that within the total solid content, the proportion of 17β-estradiol would be 10.5% by weight, that of lactic acid 5.0% by weight and that of isopropyl myristate 5.0% by weight. This mixture was uniformly stirred in a dissolver, and the percutaneous preparation was then obtained by the same process as was used in Example 1.

Example 9

To the polymer solution (i.e., the solution of adhesive material) obtained in Example 1, 17β-estradiol and fumaric acid were added so that the proportion of solids in the solution (i.e., the sum of the aforesaid constituents and the polymer) would be 22% by weight, and so that within the total solid content, the proportion of 17β-estradiol would be 10.5% by weight and that of fumaric acid would be 5.0% by weight. This mixture was uniformly stirred in a dissolver, and the percutaneous preparation was then obtained by the same process as was used in Example 1.

Example 10

To the polymer solution (i.e., the solution of adhesive material) obtained in Example 1, 17β-estradiol, fumaric acid and isopropyl myristate were added so that the proportion of solids in the solution (i.e., the sum of the aforesaid constituents and the polymer) would be 25% by weight, and so that within the total solid content, the proportion of 17β-estradiol would be 10.5% by weight, that of fumaric acid 5.0% by weight and that of isopropyl myristate 5.0% by weight. This mixture was uniformly stirred in a dissolver, and the percutaneous preparation was then obtained by the same process as was used in Example 1.

Example 11

To the polymer solution (i.e., the solution of adhesive material) obtained in Example 1, 17β-estradiol and citric acid were added so that the proportion of solids in the solution (i.e., the sum of the aforesaid constituents and the polymer) would be 22% by weight, and so that within the total solid content, the proportion of 17β-estradiol would be 10.5% by weight and that of citric acid would be 5.0% by weight. This mixture was uniformly stirred in a dissolver, and the percutaneous preparation was then obtained by the same process as was used in Example 1.

Example 12

To the polymer solution (i.e., the solution of adhesive material) obtained in Example 1, 17β-estradiol, citric acid and isopropyl myristate were added so that the proportion of solids in the solution (i.e., the sum of the aforesaid constituents and the polymer) would be 22% by weight, and so that within the total solid content, the proportion of 17β-estradiol would be 10.5% by weight, that of citric acid 5.0% by weight and that of isopropyl myristate 5.0% by weight. This mixture was uniformly stirred in a dissolver, and the percutaneous preparation was then obtained by the same process as was used in Example 1.

Example 13

To the polymer solution (i.e., the solution of adhesive material) obtained in Example 1, 17β-estradiol and O-lauryl(tetraoxyethyl)sodiumphosphate were added so that the proportion of solids in the solution (i.e., the sum of the aforesaid constituents and the polymer) would be 22% by weight, and so that within the total solid content, the proportion of 17β-estradiol would be 10.5% by weight and that of the O-lauryl(tetraoxyethyl)sodiumphosphate would be 5.0% by weight. This mixture was uniformly stirred in a dissolver, and the percutaneous preparation was then obtained by the same process as was used in Example 1.

Example 14

To the polymer solution (i.e., the solution of adhesive material) obtained in Example 1, 17β-estradiol, O-lauryl(tetraoxyethyl)sodiumphosphate together with isopropyl myristate were added so that the proportion of solids in the solution (i.e., the sum of the aforesaid constituents and the polymer) would be 22% by weight, and so that within the total solid content, the proportion of 17β-estradiol would be 10.5% by weight, that of O-lauryl(tetraoxyethyl)sodiumphosphate 5.0% by weight and that of isopropyl myristate 5.0% by weight. This mixture was uniformly stirred in a dissolver, and the percutaneous preparation was then obtained by the same process as was used in Example 1.

Comparative Example 1

By use of 188.7 g (35 mol %) of EHA and 211.3 g (65 mol %) of VP, a polymer was prepared in the same manner as indicated in Example 1, and thereafter four percutaneous preparations were prepared by the same procedure as used in Example 1, except that the proportion of 17β-estradiol in the preparations were adjusted to 16, 18, 20 and 22% by weight, respectively.

Comparative Example 2

By use of 377.5 g (85 mol %) of EHA and 40.1 g (15 mol %) of VP, a polymer was prepared in the same manner as indicated in Example 1, and thereafter four percutaneous preparations were prepared by the same procedure as used in Example 1, except that the proportion of 17β-estradiol in the preparations were adjusted to 4, 6, 8 and 10.5% by weight, respectively.

Comparative Example 3

By use of 306.4 g (80 mol %) of EHA, 41.2 g (10 mol %) of 2-ethylhexyl methacrylate (EHMA), 52.4 g (10 mol %) of dodecyl methacrylate, and 80 mg (0.02 mol %) of 1,6-hexaneglycol dimethacrylate, polymerization was carried out in the same manner as indicated in Example 1. By use of the polymer so obtained, four varieties of percutaneous preparations were obtained by adjusting the proportion of estradiol in the solid constituents to 0.1, 0.3, 4.0 and 10.5% by weight, respectively.

TABLE 1

| | EHA (mol %) | VP (mol %) | 17β-Estradiol (wt %[1]) | Absorption accelerating agents (wt %) | | |
|---|---|---|---|---|---|---|
| | | | | Agents | | Isopropyl myristate |
| Example 1 | 65 | 35 | 10.5 | — | | — |
| | | | 12.0 | | | |
| | | | 15.0 | | | |
| Example 2 | 45 | 45 | 10.5 | — | | — |
| | | | 12.0 | | | |
| | | | 15.0 | | | |
| Example 3 | 65 | 35 | 10.5 | — | | 5.0 |
| Example 4 | 65 | 35 | 10.5 | N-Lauroylsarcosine | 3.0 | 3.0 |
| Example 5 | 65 | 35 | 10.5 | Myristyl lactate | 5.0 | — |
| Example 6 | 65 | 35 | 10.5 | Myristyl lactate | 3.0 | 5.0 |
| Example 7 | 65 | 35 | 10.5 | Lactic acid | 5.0 | — |
| Example 8 | 65 | 35 | 10.5 | Lactic acid | 5.0 | 5.0 |
| Example 9 | 65 | 35 | 10.5 | Fumaric acid | 5.0 | — |
| Example 10 | 65 | 35 | 10.5 | Fumaric acid | 5.0 | 5.0 |
| Example 11 | 65 | 35 | 10.5 | Citric acid | 5.0 | — |
| Example 12 | 65 | 35 | 10.5 | Citric acid | 5.0 | 5.0 |
| Example 13 | 65 | 35 | 10.5 | O-lauryl (tetraoxyethyl) sodiumphosphate | 5.0 | — |
| Example 14 | 65 | 35 | 10.5 | O-lauryl (tetraoxyethyl) sodiumphosphate | 5.0 | 5.0 |
| Comparative Example 1 | 35 | 65 | 16.0 | — | | — |
| | | | 18.0 | | | |
| | | | 20.0 | | | |
| | | | 22.0 | | | |
| Comparative Example 2 | 85 | 15 | 4.0 | — | | — |
| | | | 6.0 | | | |
| | | | 8.0 | | | |
| | | | 10.5 | | | |
| Comparative Example 3 | 80 | — | 0.1 | — | | — |
| | | | 0.3 | | | |
| | | | 4.0 | | | |
| | | | 10.5 | | | |

[1] Percent by weight based on the adhesive base material.

Experimental Example 1

By use of the percutaneous pharmaceutical preparations obtained in the aforesaid Examples 1 and 2 and Comparative Examples 1-3, the saturated solubility of 17β-estradiol in the adhesive layers of the preparations was evaluated.

Evaluation of saturated solubility was performed in the following manner. A portion of the release paper on the preparation was detached, finely pulverized 17β-estradiol was placed on the adhesive surface of the preparation, the detached release paper was stuck back onto the surface, then the preparation was enclosed in a bag made from an aluminum laminate film, this was stored for one month at room temperature, and the saturated solubility was then evaluated by the observation of crystal growth with an optical microscope at 200× magnification.

By use of the percutaneous pharmaceutical preparations obtained in the aforesaid Examples 1 and 2 and Comparative Examples 1-3, the adhesive properties of the preparations was evaluated.

Adhesive properties were evaluated by measuring the ball tack value in accordance with the testing procedures for adhesive tape and adhesive sheets specified by JIS-Z0237 at room temperature immediately after the production of the pharmaceutical preparation.

The results of these tests are shown in Table 2. In the column indicating crystal growth, the circles indicate that crystal growth was not observed, the triangles indicate that crystal growth was uncertain, and the crosses indicate that crystal growth was observed clearly. In the column indicating adhesive properties, the circles indicate good adhesive characteristics while the crosses indicate unsatisfactory adhesion.

TABLE 2

| | Estradiol (Wt %) | Crystal growth | Adhesive properties |
|---|---|---|---|
| Example 1 | 10.5 | ○ | ○ |
| | 12.0 | ○ | ○ |
| | 15.0 | △ | ○ |
| Example 2 | 10.5 | ○ | ○ |
| | 12.0 | ○ | ○ |
| | 15.0 | ○ | ○ |
| Comparative Example 1 | 16.0 | ○ | X |
| | 18.0 | △ | X |
| | 20.0 | X | X |
| | 22.0 | X | X |
| Comparative Example 2 | 4.0 | ○ | ○ |
| | 6.0 | ○ | ○ |
| | 8.0 | △ | X |
| | 10.5 | X | X |
| Comparative Example 3 | 0.1 | ○ | ○ |
| | 0.3 | △ | ○ |
| | 4.0 | X | X |
| | 10.5 | X | X |

Table 2 shows that the percutaneous pharmaceutical preparation of the present invention can maintain a comparatively high concentration of estradiol in a dissolved state for a long period of time, and possess excellent adhesive properties. By contrast, the percutaneous pharmaceutical preparation of Comparative Example 1 containing a high proportion of VP in the adhesive base material, had poor adhesive properties. On the other hand, the preparation of Comparative Example 2 containing a high proportion of EHA in the adhesive base material (and a low proportion of VP) as well as the preparation in Comparative Example 3, using an adhesive base material synthesized from acrylate monomers only, had poor estradiol solubility.

Experimental Example 2

Pharmaceutical preparations obtained in Examples 1-14 and Comparative Examples 2 and 3 with a 17β-estradiol content of 10.5% by weight were used in this experiment. The 17β-estradiol content in each of these preparations was 4 mg/10 cm². As Comparative Example 4, the commercially available estradiol preparation, Estraderm 0.05 (manufactured by Ciba-Geigy, Switzerland; having the same structure as the preparation disclosed in Japanese Laid-Open Patent Publication No. 57-154122) was used.

The percutaneous pharmaceutical preparations obtained in the above-described examples of the present invention and comparative examples as well as the aforesaid Estraderm (after opening the sealed aluminum package of the latter) were stored under exposure to air for 30 days. At the end of this storage period, the crystal growth of 17β-estradiol was examined with an optical microscope at a magnification of 200×. The results obtained are shown in Table 3.

TABLE 3

|  | Crystal formation |
| --- | --- |
| Example 1 | Not observed |
| Example 2 | Not observed |
| Example 3 | Not observed |
| Example 4 | Not observed |
| Example 5 | Not observed |
| Example 6 | Not observed |
| Example 7 | Not observed |
| Example 8 | Not observed |
| Example 9 | Not observed |
| Example 10 | Not observed |
| Example 11 | Not observed |
| Example 12 | Not observed |
| Example 13 | Not observed |
| Example 14 | Not observed |
| Comparative Example 2 | Observed |
| Comparative Example 3 | Observed |
| Comparative Example 4 | Not observed |

Next, by use of these preparations, the degree of skin penetration by the active ingredient was evaluated. A diffusion cell 10 with the structure shown in FIG. 1 was provided. This diffusion cell 10 possesses a receptor vessel 1 of cylindrical form with a base and a donor vessel 2 of cylindrical form having a base with a orifice 21. The donor vessel 2 was superposed upon the receptor vessel 1 and the two vessels were fastened together in an airtight and concentric fashion by means of a pair of O-rings 31 and 32. The receptor vessel 1 possesses a sampling duct 11 projecting laterally from the side of the vessel. The skin sample 4 used in the test was sandwiched between the O-rings 31 and 32, and completely covered the orifice 21 of the donor vessel 2.

Figure 1:
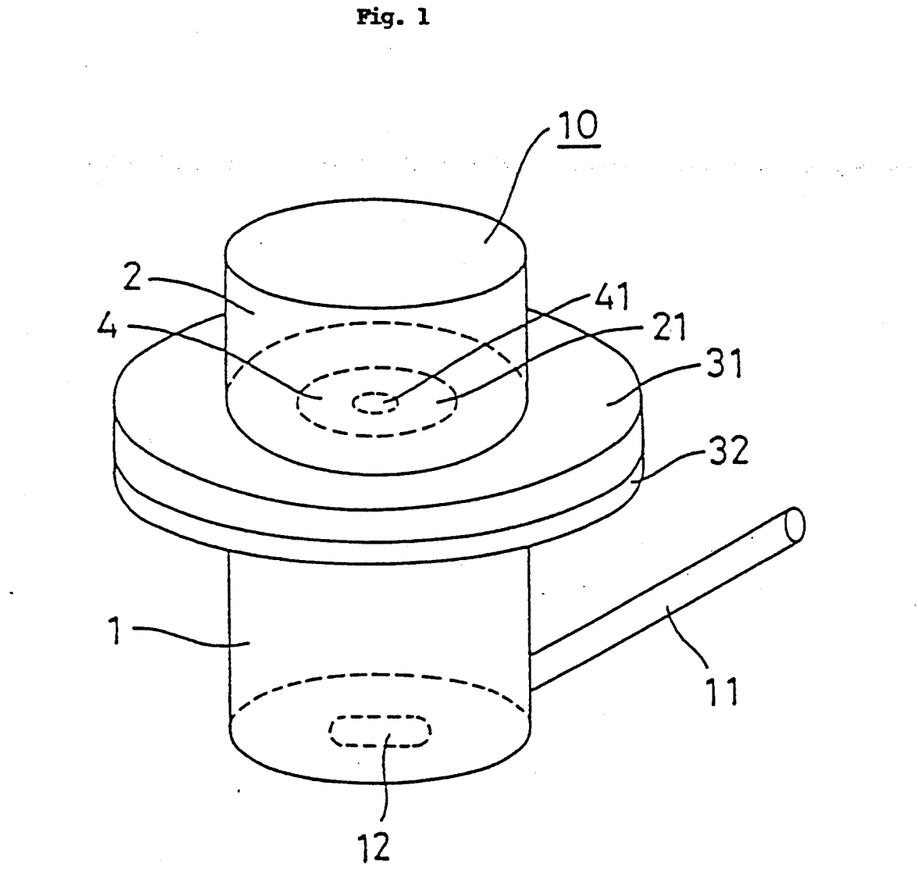
FIG. 1 is a perspective view of the diffusion cell used for testing the cutaneous penetration of the active ingredient contained in various percutaneous pharmaceutical preparations in tape form.
Figure 2:
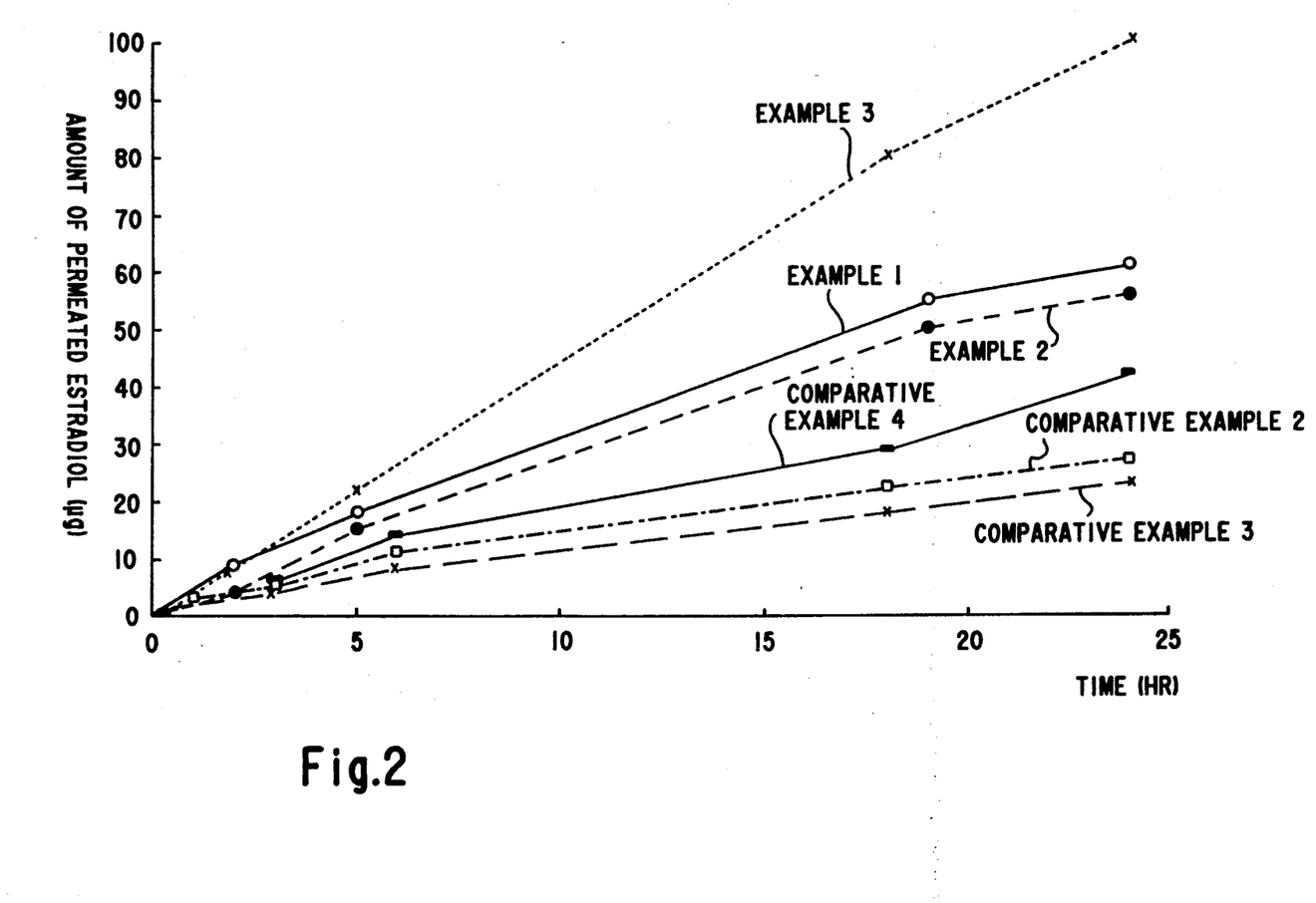
FIGS. 2 to 7 are graphs showing the rates of percutaneous permeation of estradiol from the preparations of this invention and from other preparations.
Figure 3:
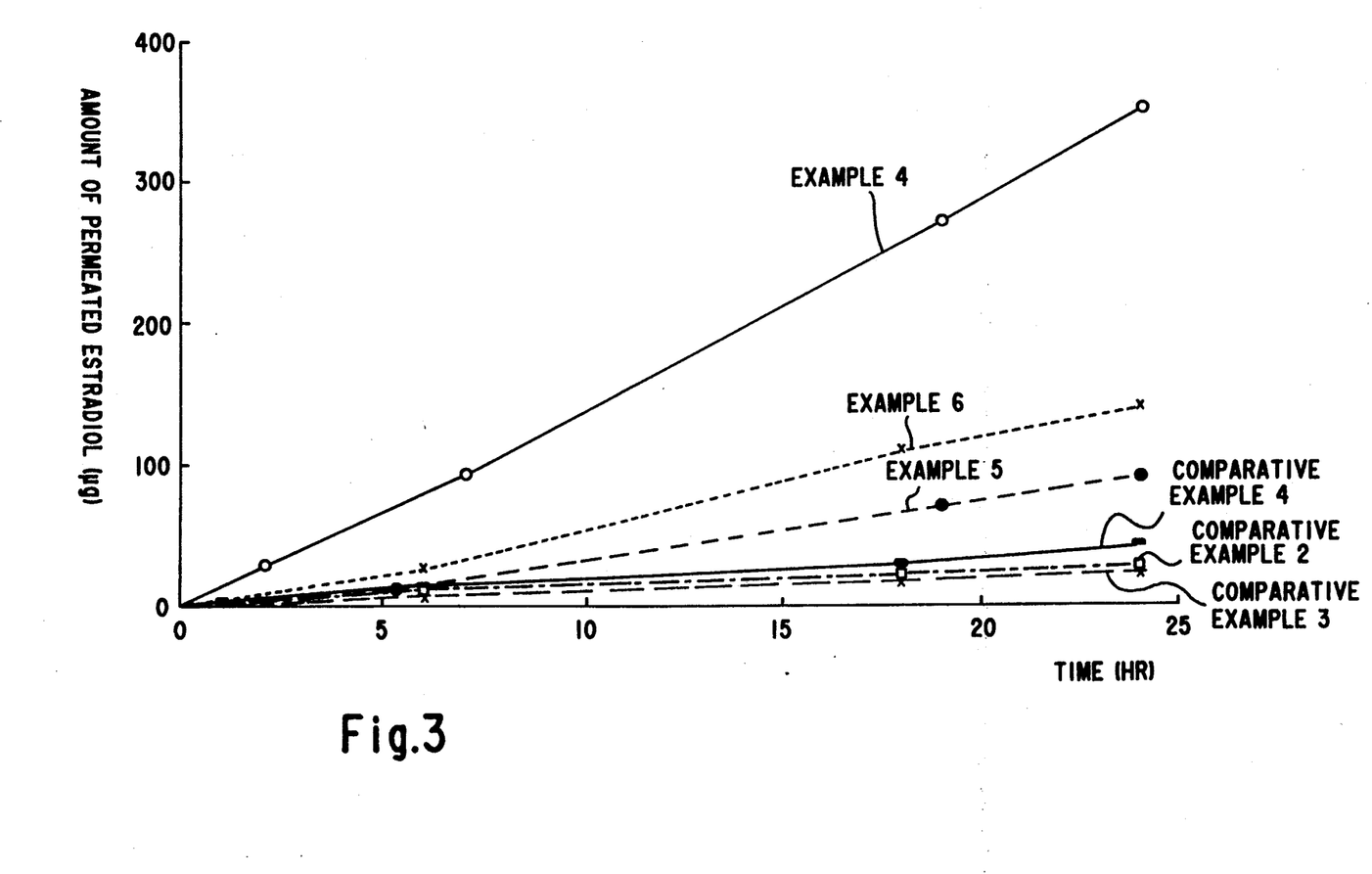
Figure 4:
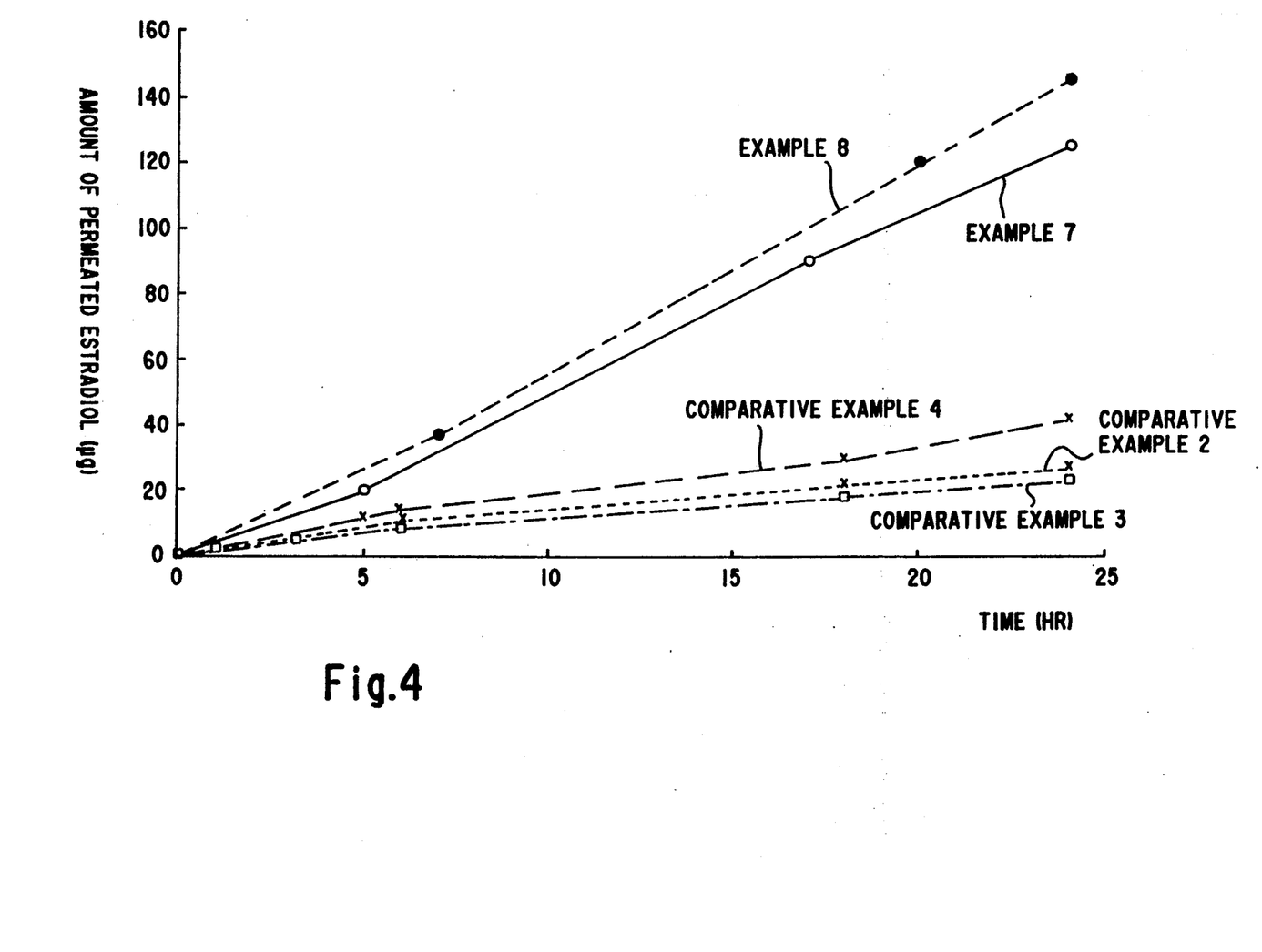
Figure 5:
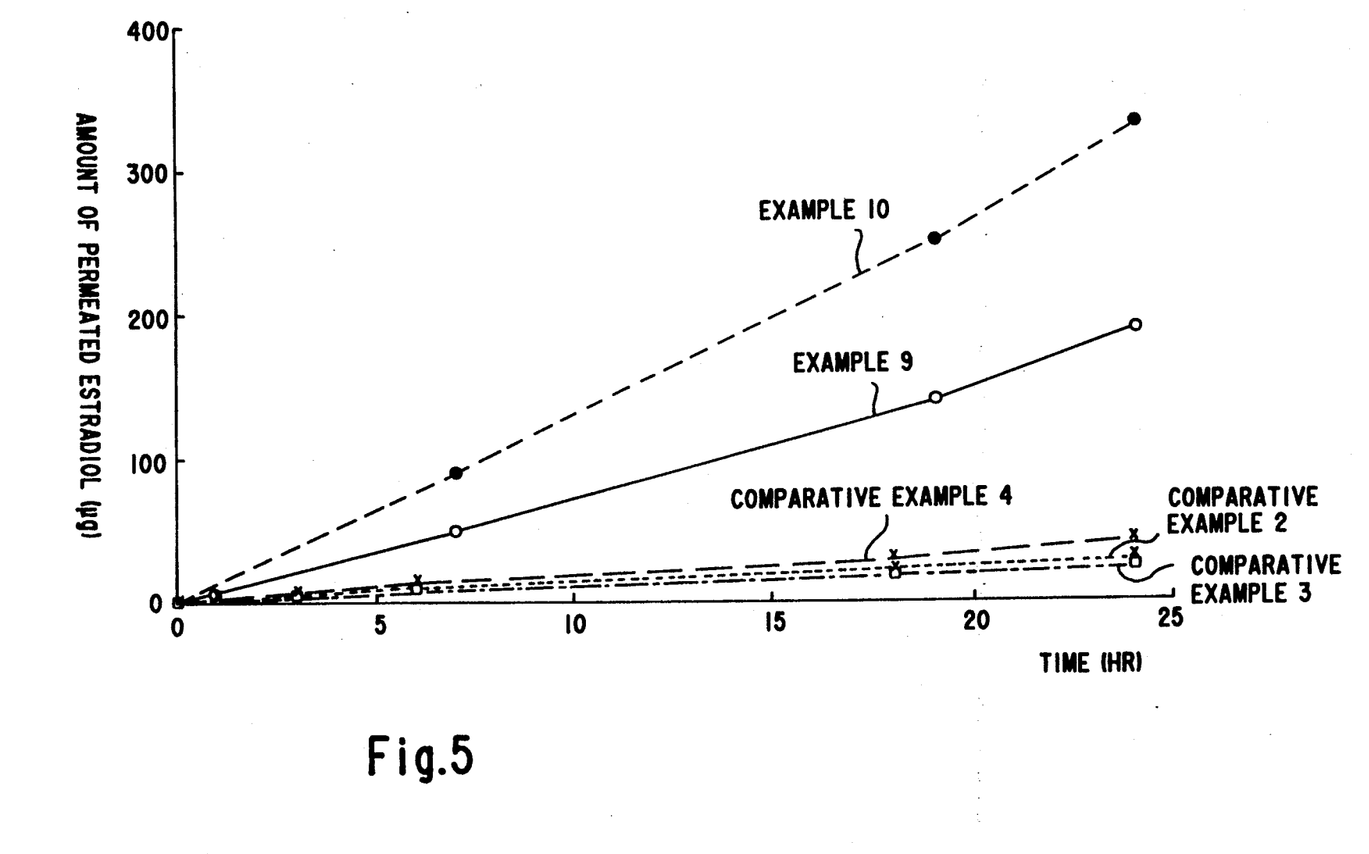
Figure 6:
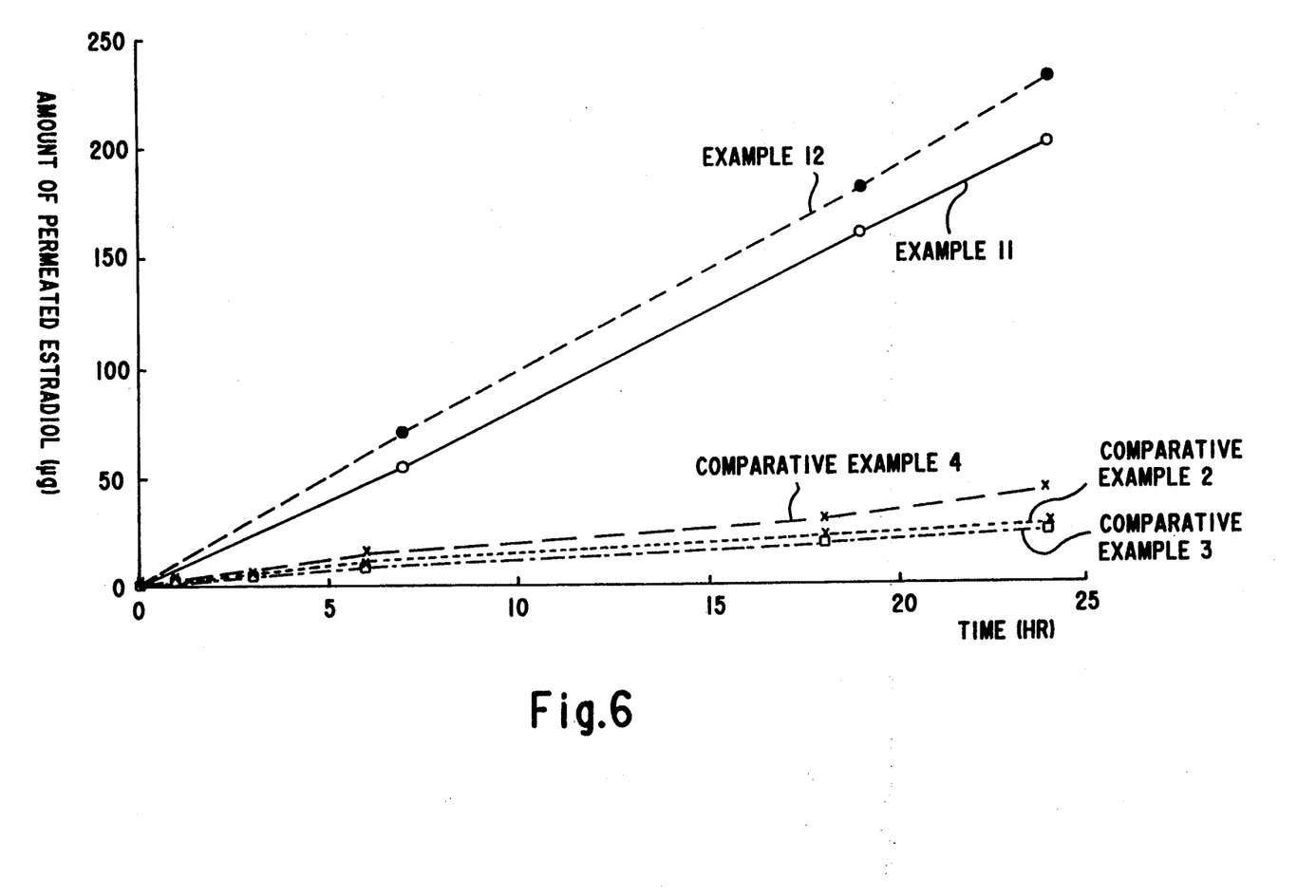
Figure 7:
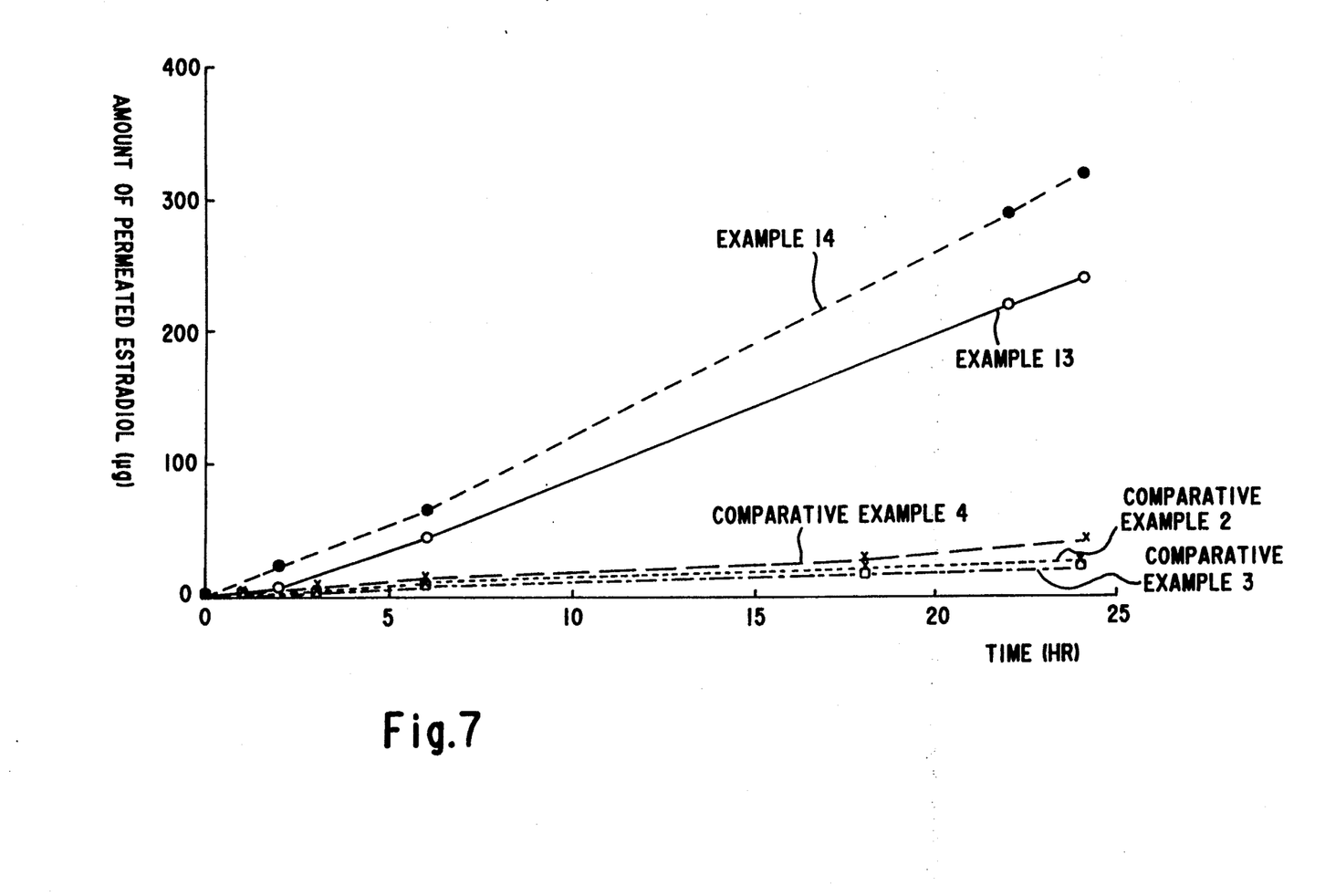

A hairless mouse (male, 6 weeks of age) was sacrificed by dislocation of the cervical vertebrae, the skin was detached, the panniculus adiposus was removed, and thus skin specimens of approximately 5 cm×5 cm in size were obtained. One of the aforesaid preparations (10 cm²) was applied to the specimen, and this was then set between the two O-rings 31 and 32 in the aforesaid diffusion cell. The receptor vessel 1 was filled with the receptor solution described below, and this receptor solution was stirred with an agitator 12.

Preparation of Receptor Solution

A buffer solution consisting of $5 \times 10^{-4}$M $NaH_2PO_4$, $2 \times 10^{-4}$M $Na_2HPO_4$, $1.5 \times 10^{-1}$M NaCl and 10 ppm of gentamicin in distilled water was adjusted to pH 7.2 with an aqueous sodium hydroxide solution, and the receptor solution was obtained by addition of polyethylene glycol 400 so that the concentration of the polyethylene glycol should be 20% by weight.

The diffusion cell 10 was placed in a temperature bath maintained at 37° C., and a 1 ml aliquot of the receptor solution was sampled through the sampling duct 11 at predetermined times, and this sample solution was replaced by 1 ml of fresh receptor solution. The drug concentration of each sample of receptor solution was measured, and the amount of permeated drug was calculated. This test was performed for 3 specimens of each type of preparation, and the average of the 3 values so obtained was calculated. The results of these tests are shown in FIGS. 2 to 7.

FIGS. 2 to 7 indicate that the percutaneous pharmaceutical preparation of the present invention are superior to those of each Comparative Example with respect to the rate of percutaneous permeation of 17β-estradiol. Moreover, the preparations of the present invention can maintain their excellent characteristics during storage even without special conditions such as hermetical sealing, etc.

Experimental Example 3

Percutaneous pharmaceutical preparation (10 cm²) of the same type as those used in Experimental Example 2 were applied to the arms of three human subjects (healthy males), and were then detached and recovered after 72 hours. The recovered preparations were subjected to methanol extraction and the concentrations of 17β-estradiol were measured with high performance liquid chromatography. In the case of Comparative Example 4, after detachment, the preparation was cut into small fragments before methanol extraction. The amount of residual drug in the preparation after detachment was then calculated from the measured estradiol concentrations, and the difference between the measured amount and the initial estradiol content of the preparation was regarded as the amount of estradiol which had been transferred percutaneously. The amount of percutaneously transferred estradiol for each preparations are shown in Table 4.

TABLE 4

|  | Amount of percutaneously transferred estradiol (μg/day) |
| --- | --- |
| Example 1 | 100 |
| Example 2 | 90 |
| Example 3 | 120 |
| Example 4 | 300 |
| Example 5 | 180 |
| Example 6 | 250 |
| Example 7 | 220 |
| Example 8 | 300 |
| Example 9 | 160 |
| Example 10 | 200 |
| Example 11 | 150 |
| Example 12 | 180 |
| Example 13 | 150 |
| Example 14 | 180 |
| Comparative Example 2 | 30 |
| Comparative Example 3 | 35 |
| Comparative Example 4 | 40 |

Table 4 shows that, for a given area and a given time, the amount of drug percutaneously transferred from the preparations of the present invention were far greater than the corresponding amount for the Comparative Example.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A percutaneous pharmaceutical preparation comprising a flexible backing, which is not permeable to an active ingredient, and an adhesive layer formed on said flexible backing; said adhesive layer comprising an adhesive base material and an active ingredient compatible with said adhesive base material;

wherein said adhesive base material consists essentially of a copolymer containing 2-ethylhexyl acrylate in a concentration of 55 to 60 mol % and N-vinyl-2-pyrrolidone in a concentration of 30 to 45 mol %, and said active ingredient is estradiol and/or the esters thereof which are contained in a concentration of 6 to 25% by weight of the total amount of said adhesive base material and said active ingredient wherein the estradiol and/or the esters thereof are completely dissolved in said copolymer.

2. A pharmaceutical preparation according to claim 1, wherein said adhesive layer contains a percutaneous absorption accelerating agent.

3. A pharmaceutical preparation according to claim 2, wherein said accelerating agent comprises an ester of higher fatty acid obtained from a higher fatty acid with 10 to 18 carbon atoms and an alcohol with 1 to 20 carbon atoms.

4. A pharmaceutical preparation according to claim 2 or 3, wherein said accelerating agent comprises a compound containing at least one amide bond.

5. A pharmaceutical preparation according to claim 2 or 3, wherein said accelerating agent comprises an ester of lactic acid obtained from lactic acid and an alcohol with 1 to 20 carbon atoms.

6. A pharmaceutical preparation according to claim 2 or 3, wherein said accelerating agent comprises lactic acid and/or the salts thereof.

7. A pharmaceutical preparation according to claim 2 or 3, wherein said accelerating agent comprises a dicarboxylic acid with 2 to 10 carbon atoms and/or the salts thereof.

8. A pharmaceutical preparation according to claim 7, wherein said dicarboxylic acid is fumaric acid.

9. A pharmaceutical preparation according to claim 2 or 3, wherein said accelerating agent comprises citric acid and/or the salts thereof.

10. A pharmaceutical preparation according to claim 2 or 3, wherein said accelerating agent comprises O-alkyl-(polyoxyethyl) phosphate and/or the salts thereof.

* * * * *

UNITED STATES PATENT AND TRADEMARK OFFICE
CERTIFICATE OF CORRECTION

PATENT NO. : 5,200,190
DATED : April 6, 1993
INVENTOR(S) : Azuma et al

It is certified that error appears in the above-indentified patent and that said Letters Patent is hereby corrected as shown below:

Column 15, line 27, "60" should be --70 --.

Signed and Sealed this

Fifth Day of March, 1996

Attest:

BRUCE LEHMAN

*Attesting Officer*  *Commissioner of Patents and Trademarks*